United States Patent [19]

Toy et al.

[11] 4,321,359
[45] Mar. 23, 1982

[54] PERFLUOROCOMPOUNDS

[75] Inventors: Madeline S. Toy, Palo Alto; Roger S. Stringham, Woodside, both of Calif.

[73] Assignee: The United States of America as represented by the Secretary of the Air Force, Washington, D.C.

[21] Appl. No.: 182,562

[22] Filed: Aug. 29, 1980

[51] Int. Cl.³ .............................................. C08G 61/02
[52] U.S. Cl. .................................. 528/397; 568/634; 568/665
[58] Field of Search ................. 528/397; 568/634, 665

[56] References Cited

U.S. PATENT DOCUMENTS

| | | | |
|---|---|---|---|
| 2,982,786 | 5/1961 | McCabe | 260/611 |
| 3,242,218 | 3/1966 | Miller | 260/615 |
| 3,397,191 | 8/1968 | Beckerbaur | 260/80.3 |
| 3,435,078 | 3/1969 | Nycgka et al. | 260/615 |
| 3,514,487 | 5/1970 | Anello et al. | 260/614 |
| 4,024,192 | 5/1977 | Benninger et al. | 260/611 R |
| 4,149,016 | 4/1979 | Toy et al. | 260/611 |

FOREIGN PATENT DOCUMENTS 990980  5/1965  United Kingdom ............... 528/397

OTHER PUBLICATIONS

Toy et al., J. of (Fluorine Chemistry, 12 (1978), 23–39 this reference has improper citation, it should read "vol. 13" (1979), Discloses Perfluoroethers from Hexafluorobenzene.

Toy et al., J. of Polymer Science: Polymer Letters Edition, 17 561–565 (1979) Discloses Copolymerization of Pentafluoropyridine.

Toy et al., J. of Polymer Science: Polymer Chemistry Edition, 16 2781–2795 (1978) Discloses Perfluorocarbocylic Ethers and Polyethers from Hexafluorobenzene.

Toy et al., J. of Fluorine Chemistry, 13 (1979), 463–464, Discloses Thermal Isomization of a Perfluorobicyclo [2,2,0] Hexene Derivative.

Primary Examiner—Wilbert J. Briggs, Sr.
Attorney, Agent, or Firm—Donald J. Singer; William J. O'Brien

[57] ABSTRACT

A method for polymerizing octafluoronaphthalene and the resulting perfluorocompounds prepared therefrom. Polymerization is accomplished by reacting the octafluoronaphthalene monomer with a mono or difluoroxyperfluoroalkane.

4 Claims, No Drawings

PERFLUOROCOMPOUNDS

STATEMENT OF GOVERNMENT INTEREST

The invention described herein may be manufactured and used by or for the Government for governmental purposes without the payment of any royalty thereon.

BACKGROUND OF THE INVENTION

This invention relates to novel perfluoropolymers and to methods for their preparation. In a more particular aspect, this invention concerns itself with methods for the polymerization of octafluoronaphthalene and to the novel compounds prepared thereby. The resultant reaction products are useful in a wide variety of electrical, chemical and aerospace applications. They are inert, low melting solids with thermal stability as well as excellent adhesivness to glass and untreated Teflon and metal surfaces. They can also be used as precursors in the synthesis of polyfunctional fluorocarbons.

The present interest in the utilization of fluorocarbon compounds for a number of industrial applications has spawned a considerable research effort in an attempt to provide new compounds and novel routes of synthesis. For example, it is known that elemental fluorine will homopolymerize hexafluorobenzene and pentafluoropyridine to mainly a hexafluorocyclohexadienyl liquid oligomer and a perfluoroazacyclohexadienyl glassy solid respectively. The copolymerizability of bis(fluoroxy) difluoromethane with perfluoroaromatic ($C_6F_6$), perfluoro-N-heteroaromatic ($C_5F_5N$), and para-bonded perfluoroaromatic (Dewar $C_6F_6$) is also known. The purpose was to interpose stable —$OCF_2O$— linking groups between six-membered ring moieties. For example, moieties were generated from copolymerizing with hexafluorobenzene, with pentafluoropyridine, and with hexafluorobicyclo [2.2.0]hexa-2,5-diene. These copolymers, however, did not form simple alternate microstructures due to concurrent fluorination and pendant perfluoro-1,3-dioxolane ring formation.

In an attempt to overcome this problem, the research effort referred to above, was maintained and it was unexpectedly discovered that even more interesting and useful products could be synthesized by effecting the polymerization of octafluoronaphthalene by reacting it with mono- and difluoroxyperfluoroalkanes. It was found that the octafluoronaphthalene monomer could be readily homopolymerized in the presence of monofluoroxyperfluoroalkane $CF_3OF$ and copolymerized with difluoroxyperfluoroalkane, $CF_2(OF)_2$ through aromatic nuclear addition reactions.

SUMMARY OF THE INVENTION

The present invention concerns itself with the polymerization of octafluoronaphthalene and to novel aromatic nuclear addition reactions. These reactions take place between the octafluoronaphthalene monomer and a monofluoroxyperfluoroalkane to produce a homopolymer; and between the monomer and a difluoroxyperfluoroalkane to produce a copolymer. The resulting perfluorobicyclic compounds provide new and useful products which are inert, low melting perfluoropolymer solids with thermal stability. They exhibit moiety unsaturation between carbons common to both rings which provide cross-linking sites. This makes them especially useful as precursors in the synthesis of polyfunctional fluorocarbons. The novel $C_{10}F_8$–$CF_2(OF)_2$ copolymer also exhibits good adhesion to glass and untreated Teflon and metal surfaces.

Accordingly, the primary object of this invention is to provide routes for the synthesis of perfluorobicyclic polymers.

Another object of this invention is to provide for the polymerization of octafluoronaphthalene by effecting aromatic nuclear addition reactions between the octafluoronaphthalene monomer and a mono or difluoroxyperfluoroalkane.

Still another object of this invention is to provide for the synthesis of novel perfluorobicyclic compounds that are especially useful as precursors because they exhibit unsaturation only between the carbons common to both rings.

The above and still other objects and advantages of this invention will become more readily apparent upon consideration of the following detailed description of its preferred embodiments.

DESCRIPTION OF THE PREFERRED EMBODIMENTS

In accordance with this invention it has been found that the above-mentioned objects can be accomplished by effecting the solution polymerization of monomeric octafluoronaphthalene ($C_{10}F_8$) in the presence of a mono or difluoroxyperfluoroalkane. The polymerization of $C_{10}F_8$ is accomplished by adding $CF_3OF$ or $CF_2(OF)_2$ at a mole ratio of about 1:2 or 1:3. This yields an almost quantitative glassy solid without fragmentation of $C_{10}F_8$. The $C_{10}F_8$ homopolymer is linked by carbon-to-carbon bond of the $C_{10}$ moieties, which contain pendant trifluoromethoxy groups. On the other hand, the copolymer is linked by —$OCF_2O$— linking groups between the $C_{10}$ moieties as well as carbon-to-carbon bonds. The latter $C_{10}$ moieties contain the pendant perfluoro-1,3-dioxolane rings. The bulk of these polymers retain double bonds between the carbons common to both rings.

The invention is further shown by the following examples which depict specific embodiments thereof.

EXAMPLE I

Octafluoronaphthalene (4.0 g, 14.7 mmole), perfluoro-2-butyltetrahydrofuran solvent (25 ml), and a magnetic stir bar encapsulated in Teflon TFE were placed in a Pyrex reaction vessel which was attached to a copper vacuum line, evacuated at −196° C., warmed to ambient temperature, and stirred to a white suspension. $CF_3OF$ (47.0 mmole) was slowly added with stirring at room temperature for 6 hr and progressively warmed to 100° C. for 2 hr. At that time, the solution absorption of $CF_3OF$ ceased. The suspension turned to a clear liquid during the initial phase of $CF_3OF$ addition at room temperature. Then a sequence of color changes was observed from clear yellowish, pinkish, greenish, and back to clear yellowish solution, which was evacuated at 100° C. to give a clear glassy solid of almost quantitative yield. The volatile condensate in the liquid-nitrogen-cooled trap was analyzed by infrared spectroscopy to consist mainly of the inert solvent in the presence of a small amount of carbonyl fluoride and silicon tetrafluoride. This volatile mixture was not investigated further. The residual solid flowed at a temperature below 50° C. with glass transition temperature at −2° C. and softening temperature at 11° C. and was soluble in hexafluorobenzene and perfluoro-2-butyltetrahydrofuran. The microstructure of the homopolymer, indicated as A in Table I was elucidated by $^{19}$F-NMR. This isolated double bonds between the carbons common to both rings showed a weak absorption at 1680 cm$^{-1}$.

The following structural formula illustrates the homopolymer of this example

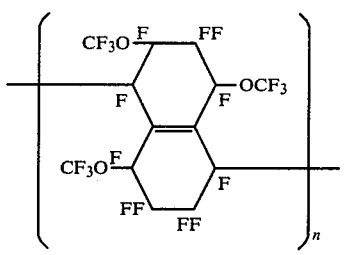
(A)

wherein n is an integer of from 2 to 20

EXAMPLE II

A procedure similar to that shown in Example I was used to copolymerize, except CF$_2$(OF)$_2$ (30.0 mmole) was added to C$_{10}$F$_8$ (3.5 g, 12.8 mmole) to give a clear yellowish transparent solid of almost quantitative yield. The resulting copolymer indicated as C in Table I flowed at a temperature below 100° C. with glass transition temperature at 10° C. and softening temperature at 28° C. and was soluble in hexafluorobenzene and perfluoro-2-butyltetrahydrofuran. Its microstructure was elucidated by $^{19}$F-NMR. The precopolymer B, (Table I) was the precursor of copolymer C, before the absorption (or pressure drop) of CF$_2$(OF)$_2$ above the polymer solution had stopped. The molecular weight of the clear liquid precopolymer B was about 2000. The double bond between the carbons common to both rings showed a weak absorption at 1680 cm$^{-1}$ and its conjugated double bonds at 1850 and 1755 cm$^{-1}$. After the complete addition of 30 mmole of CF$_2$(OF)$_2$, the residual copolymer C was a clear yellowish glassy solid with reduced unsaturation compared to the precopolymer B. The melted copolymer C was sticky and exhibited thermal stability with no detectable volatile products at 250° C.

The copolymer of this example is illustrated by the following structural formula

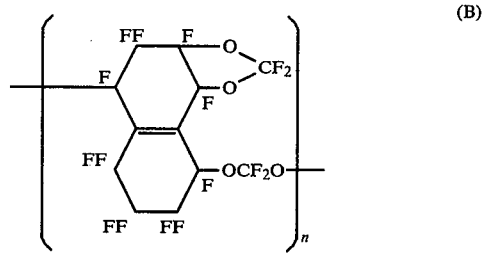
(B)

wherein n is an integer from 2 to 30.

Table I, presented hereinafter, summarizes the $^{19}$F-NMR data of the homopolymer (A) of Example 1 and copolymer (C) of Example 2.

TABLE I

| | $^{19}$F-NMR Data of C$_{10}$F$_8$ Polymers | | | |
|---|---|---|---|---|
| Polymer | Polymer Group and Assignment | Chemical Shift (ppm from CFCl$_3$) | No. of Fluorines in Polymer Group | |
| | | | Measured* | Theoretical** |
| C$_{10}$F$_8$—CF$_3$OF homopolymer-A | CF$_3$O —CF$_2$— (ring structure) | 54.4 87-160 | 85.8 73.9 | 90 82 |
| | CF—CF (ring structure) | 185-205 | 8.5 | 16 |
| C$_{10}$F$_8$—CF$_2$(OF)$_2$ precopolymer-B | —CF—CF— O O CF$_2$ | 52-56 | 10 | 10 |
| | —OCF$_2$O— —CF$_2$— (ring with —CF=CF—) | 50.5 92-144 | 3.5 34 | 4 38 |
| C$_{10}$F$_8$—CF$_2$(OF)$_2$ precopolymer-B | (naphthalene structures) | 144-158 | 4.5 | 6 |
| | CF—CF (ring structure) | 168-200 | 3 | 4 |

TABLE I-continued
$^{19}$F-NMR Data of $C_{10}F_8$ Polymers

| Polymer | Polymer Group and Assignment | Chemical Shift (ppm from CFCl$_3$) | No. of Fluorines in Polymer Group | |
|---|---|---|---|---|
| | | | Measured* | Theoretical** |
| $C_{10}F_8$—$CF_2(OF)_2$ copolymer-C | —CF—CF—<br>O     O<br>  \  /<br>  CF$_2$ | 52–62 | 10 | 10 |
| | —OCF$_2$O— | 50.5 | 8.2 | 8 |
| | —CF$_2$—<br>F  C<br> \ /<br>  C<br> / \<br>—O   C<br>—CF=CF— | 92–144 | 5.8 | 52 |
| | C    C<br> \  /<br>  CF—CF<br> /  \<br>C    C | 168–200 | 5.4 | 4 |

*Relative area.
**Based on suggested homopolymer A, where n = 1, precopolymer B and copolymer C.

The bis(fluoroxy)difluoromethane was prepared in a conventional manner such as that shown in Hohorst and Shreeve, J. Am. Chem. Soc., 89, 1809 (1967). The fluoroxytrifluoromethane and octafluoronaphthalene were purchased from PCR and perfluoro-2-butyltetrahydrofuran (FC-75) was purchased from 3M. The compounds were checked by infrared spectroscopy and used as received.

Vacuum manipulations were carried out in a copper-Monel system with a Pyrex reaction vessel. Pressures were measured with a Heise gauge (0–100 cm Hg absolute with 500 increments) of accuracy to 1 mm Hg. The amount of volatile reactant was determined by P-V-T measurements assuming ideal gas behavior.

The infrared spectra were measured on a Perkin-Elmer 567 spectrophotometer. NaCl windows were used for the liquids and solids and a 5-cm Monel gas cell fitted with AgCl windows for the gases. The $^{19}$F-NMR spectra were recorded by a Varian XL-100 spectrometer operating at 94.1 MHz and 35° C. using hexafluorobenzene as an external reference. The F chemical shifts were then converted to CFCl$_3$ as the reference using the value of 164.9 ppm for hexafluorobenzene.

Fluoroxytrifluoromethane and bis(fluoroxy)difluoromethane are potentially hazardous, although they do not appear to be sensitive to phase changes. Adequate protection shielding and caution must be practiced.

Upon oxidation of the $C_{10}F_8$ homopolymer of Example 1 with CF$_3$OF and the $C_{10}F_8$ copolymer of Example 2 with CF$_2$(OF)$_2$ preferably under alkaline conditions, perfluoropolyethers containing tertiary hydroxyl groups are formed. This is illustrated by the following equations in which equation (1) illustrate the oxidation of the homopolymer (A) of Example 1 and equation (2) illustrates the oxidation of the copolymer (B) of Example 2. The letter n represents an integer of from 1 to 20 in equation 1 and from 1 to 30 in equation 2.

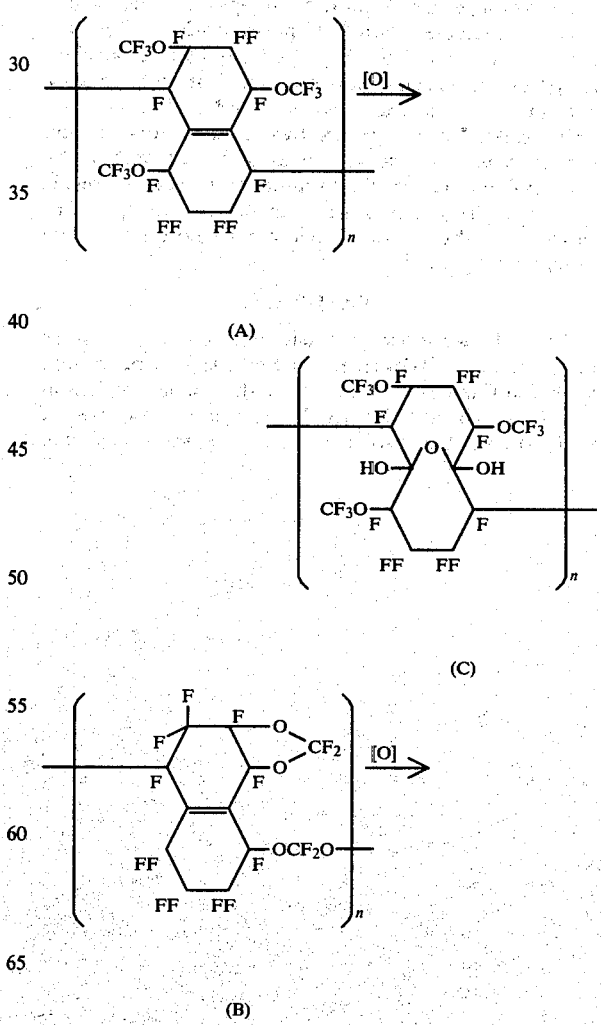

-continued

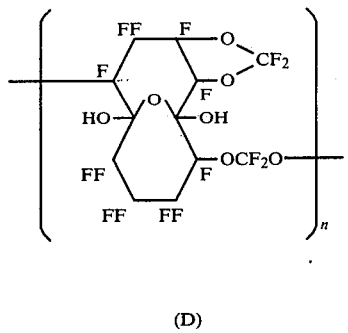

(D)

Example 3 and 4 which follow, further illustrate the oxidation of the polymers of Examples 1 and 2.

EXAMPLE 3

The homopolymer (A) of Example 1 (4.0 g) was dissolved in about 20 ml of perfluoro-2-butyltetrahydrofuran and the solution was added slowly to a stirred solution to $KMnO_4$ (1.0 g) in anhydrous acetone (50 ml) during 30 min. The mixture was stirred overnight at room temperature. Water (20 ml) was added and stirred for two hours. The perfluoro-2-butyltetrahydrofuran layer was separated from the top aqueous layer, which was then extracted with fresh perfluoro-2-butyltetrahydrofuran solvent. The combined perfluoro-2-butyltetrahydrofuran extracts was evacuated at ambient temperature to give a clear yellowish solid of almost quantitative yield. Upon exposure to air, the yellowish solid was hygroscopic and darkened to a brownish black solid, polymer having the formula shown in equation (1) as polymer (C). The infrared analysis of the polymer showed the absence of olefinic bonds and the presence of hydroxyl groups.

EXAMPLE 4

The polymer shown in equation 2 was oxidized from the copolymer (B) of Example 2 by a similar procedure to that in Example 3. The yellowish residual solid from copolymer (B) was likewise hygroscopic and darkened to a brownish black solid shown as polymer (D), which contained hydroxyl groups in the absence of olefinic bonds.

The polymers (C) and (D) of Examples 3 and 4 can also be prepared by bubbling ozone (3 to 5% in oxygen) through the perfluoro-2-butyltetrahydrofuran solutions of the polymers (A) and (B) of Examples 1 and 2 respectively.

While the invention has been described with particularity in reference to specific embodiments thereof, it is to be understood that various alterations and modifications thereof may be undertaken and that all such modifications as fall within the scope of the appended claims are intended to be included herein.

What is claimed is:

1. As a compound, the homopolymer having the formula

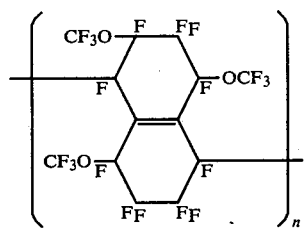

wherein n is an integer of from 2 to 20.

2. A method for preparing a perfluorobicyclic polymer which comprises the steps of (A) forming a reaction mixture of (1) octafluoronaphthalene and (2) fluoroxytrifluoromethane; (B) heating said mixture within a vacuum at a temperature and for a period of time sufficient to effect a reaction therebetween; and (C) separating the resulting homopolymer.

3. A method in accordance with claim 2 wherein the components of said mixture are present in a mole ratio of about 1:2 to 1:3.

4. A method in accordance with claim 2 wherein said reaction mixture temperature is maintained at room temperature for about six hours and progressively warmed to 100° C. for about two hours.

* * * * *